United States Patent

Yamamoto et al.

(10) Patent No.: US 10,354,099 B2
(45) Date of Patent: Jul. 16, 2019

(54) PARTICLE SIMULATION DEVICE, PARTICLE SIMULATION METHOD, AND PARTICLE SIMULATION PROGRAM

(71) Applicant: Japan Agency for Marine-Earth Science and Technology, Kanagawa (JP)

(72) Inventors: Miki Yamamoto, Yokosuka (JP); Daisuke Nishiura, Yokosuka (JP); Hide Sakaguchi, Yokosuka (JP)

(73) Assignee: Japan Agency for Marine-Earth Science and Technology, Kanagawa (JP)

( * ) Notice: Subject to any disclaimer, the term of this patent is extended or adjusted under 35 U.S.C. 154(b) by 190 days.

(21) Appl. No.: 15/315,254

(22) PCT Filed: May 29, 2015

(86) PCT No.: PCT/JP2015/065609
§ 371 (c)(1),
(2) Date: Nov. 30, 2016

(87) PCT Pub. No.: WO2015/186633
PCT Pub. Date: Dec. 10, 2015

(65) Prior Publication Data
US 2017/0193251 A1   Jul. 6, 2017

(30) Foreign Application Priority Data

Jun. 4, 2014  (JP) .................................. 2014-115567

(51) Int. Cl.
*G06G 7/48*     (2006.01)
*G16B 5/00*    (2019.01)
(Continued)

(52) U.S. Cl.
CPC ............. *G06G 7/485* (2013.01); *G06F 17/10* (2013.01); *G06F 17/5009* (2013.01); *G16B 5/00* (2019.02); *G16C 10/00* (2019.02)

(58) Field of Classification Search
None
See application file for complete search history.

(56) References Cited

U.S. PATENT DOCUMENTS

| 5,596,511 A | 1/1997 | Toyoda et al. |
| 7,948,485 B1 | 5/2011 | Larsen et al. |

(Continued)

FOREIGN PATENT DOCUMENTS

| EP | 2 509 009 A1 | 10/2012 |
| JP | 2010-238030 A | 10/2010 |

(Continued)

OTHER PUBLICATIONS

Notification of Transmittal of Copies of Translation of the International Preliminary Report on Patentability and Translation of Written Opinion of the International Searching Authority; PCT/JP2015/065609 dated Dec. 15, 2016.

(Continued)

*Primary Examiner* — Kamini S Shah
*Assistant Examiner* — Russ Guill
(74) *Attorney, Agent, or Firm* — Studebaker & Brackett PC

(57) ABSTRACT

A particle simulation device comprises: a position information acquisition unit that acquires position information for the particles; a pair setting unit that selects pairs of particles and sets a pair number, on the basis of the position information; a reference information generation unit that generates a matrix from the pair numbers and the particle numbers, and generates reference information for referencing the pair numbers from the particle numbers on the basis of a (Continued)

matrix in which the order of the rows of the matrix are sorted on the basis of the particle numbers; a sum calculation unit that calculates a sum of interaction forces for each particle on the basis of the reference information; and a particle information calculation unit that calculates the position and velocity of the particles on the basis of the sum of interaction forces.

15 Claims, 13 Drawing Sheets

(51) Int. Cl.
*G06F 17/10* (2006.01)
*G06F 17/50* (2006.01)
*G16C 10/00* (2019.01)

(56) References Cited

U.S. PATENT DOCUMENTS

| | | |
|---|---|---|
| 2012/0259602 A1 | 10/2012 | Nishiura et al. |
| 2013/0173889 A1 | 7/2013 | Shaw et al. |
| 2013/0204589 A1 | 8/2013 | Ohnishi |
| 2013/0297270 A1* | 11/2013 | Cleary ............... G06F 17/5009 703/6 |

FOREIGN PATENT DOCUMENTS

| | | |
|---|---|---|
| WO | 2010/140957 A1 | 12/2010 |
| WO | 2013/111204 A1 | 8/2013 |

OTHER PUBLICATIONS

A Notice of Allowance, "Decision to Grant a Patent," mailed by the Japanese Patent Office dated Dec. 5, 2017, which corresponds to Japanese Patent Application No. 2014-115567 and is related to U.S. Appl. No. 15/315,254; with English translation.

International Search Report; PCT/JP2015/065609 dated Jun. 30, 2015.

M. Muller et al.; "Particle-Based Fluid Simulation for Interactive Applications"; Eurographics/SIGGRAPH Symposium on Computer Animation; 2003; pp. 154-159.

D. Nishiura et al.; "High Efficiency Algorithm for DEM Simulation on GPU"; Transactions of Japan Society for Computational Engineering and Science; Jun. 1, 2010; Paper No. 20100007.

D. Nishiura et al.; "Parallel-vector algorithms for particle simulations on shared-memory multiprocessors"; Journal of Computational Physics; Mar. 1, 2011; vol. 230; pp. 1923-1938.

H. P. Zhu et al., "Discrete article simulation of particulate systems: Theoretical developments", Chemical Engineering Science 62, Mar. 23, 2007, www.elsevier.com/locate/ces, pp. 3378-3396.

The extended European search report issued by the European Patent Office on Sep. 10, 2018, which corresponds to European Patent Application No. 15803426.4-1111 and is related to U.S. Appl. No. 15/315,254.

* cited by examiner

Fig.3(a)

PARTICLE NUMBER j $$\text{PARTICLE NUMBER } i \begin{pmatrix} & 1 & 2 & 3 & 4 & 5 & 6 & 7 & 8 & 9 & 10 \\ 1 & 0 & 0 & 0 & 0 & 0 & 0 & 0 & 0 & 0 \\ 2 & & 1 & 0 & 0 & 0 & 0 & 0 & 0 & 0 \\ 3 & & & 0 & 0 & 0 & 0 & 0 & 0 & 0 \\ 4 & & & & 0 & 0 & 0 & 1 & 0 & 0 \\ 5 & & & & & 1 & 1 & 1 & 1 & 0 \\ 6 & & & & & & 1 & 1 & 1 & 0 \\ 7 & & & & & & & 1 & 1 & 0 \\ 8 & & & & & & & & 0 & 1 \\ 9 & & & & & & & & & 1 \\ 10 & & & & & & & & & \end{pmatrix}$$

Fig.3(b)

$$\text{PARTICLE NUMBER } i \begin{matrix} 1 \\ 2 \\ 3 \\ 4 \\ 5 \\ 6 \\ 7 \\ 8 \\ 9 \\ 10 \end{matrix} \begin{pmatrix} \\ 3 \\ \\ 8 \\ 6 & 4 & 8 & 9 \\ 7 & 8 & 9 \\ 8 & 9 \\ 10 \\ 10 \end{pmatrix} \begin{matrix} n_{i<j} \\ 0 \\ 1 \\ 0 \\ 1 \\ 4 \\ 3 \\ 2 \\ 1 \\ 1 \\ 0 \end{matrix} \begin{pmatrix} \\ 1 \\ 2 \\ 3 & 4 & 5 & 6 \\ 7 & 8 & 9 \\ 10 & 11 \\ 12 \\ 13 \end{pmatrix}$$

$U^{(1)}$ $\qquad$ $R^{(1)}$

Fig.3(c)

$$\begin{pmatrix} p & i & j \\ 1 & 2 & 3 \\ 2 & 4 & 8 \\ 3 & 5 & 6 \\ 4 & 5 & 7 \\ 5 & 5 & 8 \\ 6 & 5 & 9 \\ 7 & 6 & 7 \\ 8 & 6 & 8 \\ 9 & 6 & 9 \\ 10 & 7 & 8 \\ 11 & 7 & 9 \\ 12 & 8 & 10 \\ 13 & 9 & 10 \end{pmatrix} \begin{pmatrix} p & i & j \\ 1 & 2 & 3 \\ 3 & 5 & 6 \\ 4 & 5 & 7 \\ 7 & 6 & 7 \\ 2 & 4 & 8 \\ 5 & 5 & 8 \\ 8 & 6 & 8 \\ 10 & 5 & 8 \\ 6 & 5 & 9 \\ 9 & 6 & 9 \\ 11 & 7 & 9 \\ 12 & 8 & 10 \\ 13 & 9 & 10 \end{pmatrix}$$

$T^{(1)}$ $\qquad$ $T^{(2)}$

Fig.3(d)

$$\text{PARTICLE NUMBER } i \begin{matrix} 1 \\ 2 \\ 3 \\ 4 \\ 5 \\ 6 \\ 7 \\ 8 \\ 9 \\ 10 \end{matrix} \begin{pmatrix} \\ \\ 1 \\ \\ \\ 3 \\ 4 & 7 \\ 2 & 5 & 8 & 10 \\ 6 & 9 & 11 \\ 12 & 13 \end{pmatrix} \begin{matrix} n_{i>j} \\ 0 \\ 0 \\ 1 \\ 0 \\ 0 \\ 1 \\ 2 \\ 4 \\ 3 \\ 2 \end{matrix}$$

PARTICLE NUMBER j $$\text{PARTICLE NUMBER } i \begin{array}{c} 1 \\ 2 \\ 3 \\ 4 \\ 5 \\ 6 \\ 7 \\ 8 \\ 9 \\ 10 \end{array} \begin{pmatrix} & 0 & 0 & 0 & 0 & 0 & 0 & 0 & 0 & 0 \\ 0 & & 1 & 0 & 0 & 0 & 0 & 0 & 0 & 0 \\ 0 & 1 & & 0 & 0 & 0 & 0 & 0 & 0 & 0 \\ 0 & 0 & 0 & & 0 & 0 & 0 & 1 & 0 & 0 \\ 0 & 0 & 0 & 0 & & 1 & 1 & 1 & 1 & 0 \\ 0 & 0 & 0 & 0 & 1 & & 1 & 1 & 1 & 0 \\ 0 & 0 & 0 & 0 & 1 & 1 & & 1 & 1 & 0 \\ 0 & 0 & 0 & 1 & 1 & 1 & 1 & & 0 & 1 \\ 0 & 0 & 0 & 0 & 1 & 1 & 1 & 0 & & 1 \\ 0 & 0 & 0 & 0 & 0 & 0 & 0 & 1 & 1 & \end{pmatrix}$$

*Fig.6(b)*

$$\text{PARTICLE NUMBER } i \begin{array}{c} 1 \\ 2 \\ 3 \\ 4 \\ 5 \\ 6 \\ 7 \\ 8 \\ 9 \\ 10 \end{array} \overset{n_{i<j}}{\begin{pmatrix} \\ 3 \\ \\ 8 \\ 6\;7\;8\;9 \\ 7\;8\;9 \\ 8\;9 \\ 10 \\ 10 \\ \end{pmatrix}} \begin{matrix} 0 \\ 1 \\ 0 \\ 1 \\ 4 \\ 3 \\ 2 \\ 1 \\ 1 \\ 0 \end{matrix} \overset{}{\begin{pmatrix} \\ \\ 2 \\ \\ \\ 5 \\ 5\;6 \\ 4\;5\;6\;7 \\ 5\;6\;7 \\ 8\;9 \end{pmatrix}} \begin{matrix} 0 \\ 0 \\ 1 \\ 0 \\ 1 \\ 2 \\ 4 \\ 3 \\ 2 \end{matrix}$$

PARTICLE NUMBER j $$\text{PARTICLE NUMBER } i \begin{array}{c} 1 \\ 2 \\ 3 \\ 4 \\ 5 \\ 6 \\ 7 \\ 8 \\ 9 \\ 10 \end{array} \begin{pmatrix} & 0 & 0 & 0 & 0 & 0 & 0 & 0 & 0 & 0 \\ 0 & & 1 & 0 & 0 & 0 & 0 & 0 & 0 & 0 \\ 0 & 1 & & 0 & 0 & 0 & 0 & 0 & 0 & 0 \\ 0 & 0 & 0 & & 0 & 0 & 0 & 2 & 0 & 0 \\ 0 & 0 & 0 & 0 & & 3 & 4 & 5 & 6 & 0 \\ 0 & 0 & 0 & 0 & 3 & & 7 & 8 & 9 & 0 \\ 0 & 0 & 0 & 4 & 7 & & & 10 & 11 & 0 \\ 0 & 0 & 2 & 5 & 8 & 10 & & & 0 & 12 \\ 0 & 0 & 0 & 6 & 9 & 11 & 0 & & & 13 \\ 0 & 0 & 0 & 0 & 0 & 0 & 12 & 13 & & \end{pmatrix}$$

*Fig.6(d)*

$$\text{PARTICLE NUMBER } i \begin{array}{c} 1 \\ 2 \\ 3 \\ 4 \\ 5 \\ 6 \\ 7 \\ 8 \\ 9 \\ 10 \end{array} \begin{pmatrix} \\ 1 \\ \\ 2 \\ 3\;4\;5\;6 \\ 7\;8\;9 \\ 10\;11 \\ 12 \\ 13 \\ \end{pmatrix} \begin{pmatrix} \\ \\ \\ 1 \\ \\ 3 \\ 4\;7 \\ 2\;5\;8\;10 \\ 6\;9\;11 \\ 12\;13 \end{pmatrix}$$

R(1)  R(2)

PARTICLE SIMULATION DEVICE, PARTICLE SIMULATION METHOD, AND PARTICLE SIMULATION PROGRAM

TECHNICAL FIELD

The present invention relates to a particle simulation device, a particle simulation method, and a particle simulation program.

BACKGROUND ART

Particle simulation is one of fundamental simulation techniques and used for simulation of basic substances such as fluids or solids, as well as industrially important substances such as soils and powders, and biologically and medically important substances such as proteins. The applications include, for example, simulations of disasters such as landslides, liquefaction, and tsunamis, and drug discovery simulations such as protein design. Those various substance simulations are extremely valuable in application, and the progress of simulation techniques is important to promptly develop the applications.

A particle simulation embodies the movement of the entire particle group by storing the positions and velocities of individual particles as variables and tracking their changes based on a model. In particular, in the methods widely used as particle simulations, such as discrete element method (DEM) (clods, sands), smoothed particle hydrodynamics (SPH) (fluids), and molecular dynamics (MD) (molecules, proteins), the interactions between particles are simulated, and specifically the interactions are assumed to be symmetric (action-reaction law). Non-Patent Literature 1 below proposes an approach that accelerates a particle simulation using this symmetry. This approach is created for graphics processing unit (GPU) calculation so as to enable parallel calculation. In this approach, the use of symmetry is characterized in that a list of interaction pairs between particles, called a pair list, is created and used. The calculation of interactions based on this pair list reduces the entire simulation time.

CITATION LIST

Non Patent Literature

[Non-Patent Literature 1] D. Nishiura, H. Sakaguchi, Parallel-vector algorithms for particle simulations on shared-memory multiprocessors, J. Comp. Phys. 230 (2011) 1923-1938.

SUMMARY OF INVENTION

Technical Problem

In the method described in Non-Patent Literature 1, each particle is given a particle number based on the position of the particle, and each particle is paired with another particle (paired with a particle serving as a contact candidate). This pair is given a number for specifying the pair, and a contact force is calculated for each pair. In the method described above, in order to compute the sum of contact forces of each particle, a list of the numbers of pairs to which the particle of interest belongs is created for each particle.

Two such lists are created: a list of pairs with particles having larger particle numbers than the particle of interest; and a list of pairs with particles having smaller particle numbers than the particle of interest. Of these lists, in order to create the list of pairs with particles having smaller particle numbers than the particle of interest, the method described in Non-Patent Literature 1 uses an algorithm conducting a search with a double for-loop including if-statement (condition determination). This algorithm performs a number of trial-and-error processes that require many memory accesses.

Such a number of trial-and-error processes cause warp divergence to significantly reduce the computation performance of the GPU and therefore pose a serious problem when executed in the GPU.

The present invention is made in view of the problem above and aims to provide a particle simulation device, a particle simulation method, and a particle simulation program capable of improving computation efficiency.

Solution to Problem

In order to achieve the above-noted object, a particle simulation device according to an embodiment of the present invention is configured to calculate position and velocity of a plurality of particles in a workspace based on interaction force with another particle and simulate behavior of the particles. The particle simulation device includes: position information acquisition means for acquiring position information indicating a particle position, for each of the plurality of particles; particle number setting means for setting a sortable particle number for each of the plurality of particles; pair setting means for selecting a pair of particles neighboring to each other based on the position information acquired by the position information acquisition means, and setting a pair number for the pair based on the particle number of one of particles of the pair that is set by the particle number setting means; reference information generation means for generating a matrix having the pair number set by the pair setting means and the particle numbers of particles of the pair as components of a row, sorting order of a column of the matrix based on the particle number of another particle of the pair, and generating reference information for referring to the pair number of a pair including a particle by the particle number of the particle, based on the sorted matrix; interaction force calculation means for performing an interaction determination between particles related to each of pairs selected by the pair setting means and calculating interaction force between particles determined to interact; sum calculation means for calculating a sum of interaction forces for each particle, from the interaction force calculated by the interaction force calculation means, based on the reference information generated by the reference information generation means; and particle information calculation means for calculating position and velocity of a particle, based on the sum of interaction forces for each particle that is calculated by the sum calculation means.

In the particle simulation device according to an embodiment of the present invention, the sorted matrix is used to generate reference information corresponding to the above-noted list without using a double for-loop. This eliminates the need for a number of trial-and-error processes. That is, the particle simulation device according to an embodiment of the present invention can improve the computation efficiency.

The reference information generation means may set a smaller particle number of the particle numbers of particles of the pair as a component in one column of the matrix and set a larger particle number of the particle numbers of the particles of the pair as a component in another column. With this configuration, reference information can be generated based on the matrix sorted appropriately and reliably. This enables an embodiment of the present invention to be carried out appropriately and reliably.

The particle number setting means may set a sortable particle number for each of the plurality of particles based on the position information acquired by the position information acquisition means. With this configuration, particle numbers can be assigned to particles appropriately and reliably. This enables an embodiment of the present invention to be carried out appropriately and reliably.

The workspace may be divided into a plurality of cells. The position information acquisition means may acquire information indicating a cell in which a particle is positioned, for each of a plurality of particles, as position information. This configuration enables efficient and easy selection of a pair of neighboring particles and can further improve the computation efficiency.

The present invention can be not only described as the invention of a particle simulation device as mentioned above but also described as the invention of a particle simulation method and a particle simulation program as follows. The inventions are in different categories but substantially the same and achieve the same operation and effects.

More specifically, a particle simulation method according to an embodiment of the present invention is an operation method which is a method of operating a particle simulation device that is configured to calculate position and velocity of a plurality of particles based on interaction force with another particle in a workspace and simulate behavior of the particles. The particle simulation method includes: a position information acquisition step of acquiring position information indicating a particle position, for each of the plurality of particles; a particle number setting step of setting a sortable particle number for each of the plurality of particles; a pair setting step of selecting a pair of particles neighboring to each other based on the position information acquired in the position information acquisition step, and setting a pair number for the pair based on the particle number of one of particles of the pair that is set in the particle number setting step; a reference information generation step of generating a matrix having the pair number set in the pair setting step and the particle numbers of particles of the pair as components of a row, sorting order of a column of the matrix based on the particle number of another particle of the pair, and generating reference information for referring to the pair number of a pair including a particle by the particle number of the particle, based on the sorted matrix; an interaction force calculation step of performing an interaction determination between particles related to each of pairs selected in the pair setting step and calculating interaction force between particles determined to interact; a sum calculation step of calculating a sum of interaction forces for each particle from the interaction force calculated in the interaction force calculating step, based on the reference information generated in the reference information generation step; and a particle information calculation step of calculating position and velocity of a particle, based on the sum of interaction forces for each particle that is calculated in the sum calculating step.

A particle simulation program according to an embodiment of the present invention causes a computer to function as a particle simulation device that is configured to calculate position and velocity of a plurality of particles based on interaction force with another particle in a workspace and simulate behavior of the particles. The particle simulation program causes the computer to function as: position information acquisition means for acquiring position information indicating a particle position, for each of the plurality of particles; particle number setting means for setting a sortable particle number for each of the plurality of particles; pair setting means for selecting a pair of particles neighboring to each other based on the position information acquired by the position information acquisition means, and setting a pair number for the pair based on the particle number of one of particles of the pair that is set by the particle number setting means; reference information generation means for generating a matrix having the pair number set by the pair setting means and the particle numbers of particles of the pair as components of a row, sorting order of a column of the matrix based on the particle number of another particle of the pair, and generating reference information for referring to the pair number of a pair including a particle by the particle number of the particle, based on the sorted matrix; interaction force calculation means for performing an interaction determination between particles related to each of pairs selected by the pair setting means and calculating interaction force between particles determined to interact; sum calculation means for calculating a sum of interaction forces for each particle from the interaction force calculated by the interaction force calculation means, based on the reference information generated by the reference information generation means; and particle information calculation means for calculating position and velocity of a particle, based on the sum of interaction forces for each particle that is calculated by the sum calculation means.

Advantageous Effects of Invention

An embodiment of the present invention uses a sorted matrix to generate reference information corresponding to the aforementioned list without using a double for-loop, thereby eliminating the need for a number of trial-and-error processes. That is, an embodiment of the present invention can improve the computation efficiency.

BRIEF DESCRIPTION OF DRAWINGS

FIGS. 3(a) to 3(d) are diagrams showing matrices and arrays generated in the present embodiment.

FIGS. 6(a) to 6(d) are diagrams showing matrices and arrays generated in the method described in Non-Patent Literature 1.

DESCRIPTION OF EMBODIMENTS

Embodiments of a particle simulation device, a particle simulation method, and a particle simulation program according to the present invention will be described in details below in conjunction with the drawings. It should be noted that the same elements are denoted with the same reference signs in the description of the drawings, and an overlapping description is omitted.

Figure 1:
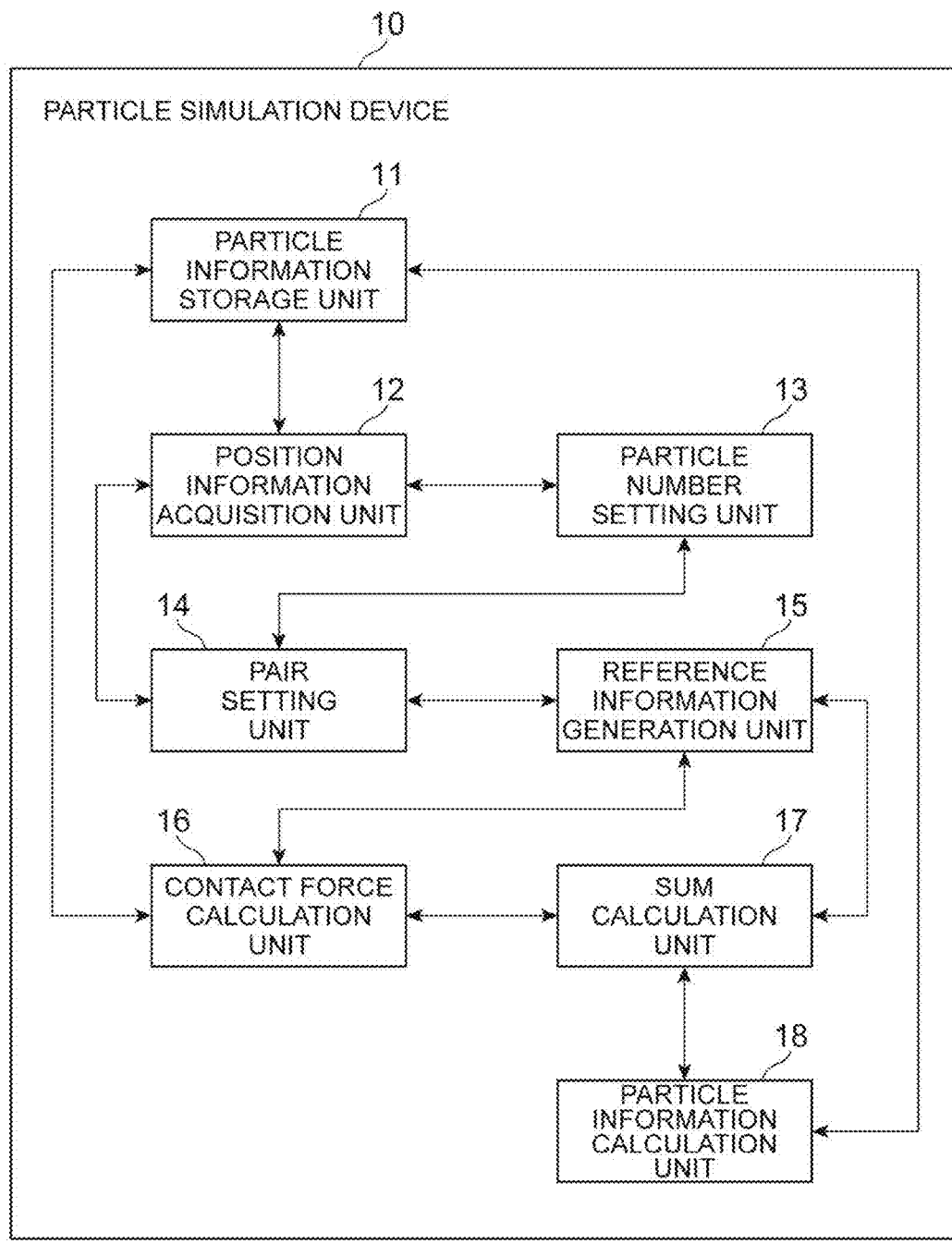
FIG. 1 is a diagram showing a functional configuration of a particle simulation device according to an embodiment of the present invention.

FIG. 1 shows a particle simulation device 10 according to the present embodiment. The particle simulation device 10 is a device that simulates (analyzes) the behavior of a plurality of spherical particles in a workspace. Specifically, the particle simulation device 10 calculates the force acting on each particle based on the position and velocity of each particle for each time (step) in the simulation. The force acting on each particle includes contact force which is interaction force caused by contact (collision) that is interaction between particles. The particle simulation device 10 calculates the position and velocity of each particle at the next time based on the calculated force.

Particles to be simulated by the particle simulation device 10 according to the present embodiment include any particles targeted by conventional particle simulations. For example, soils and powders described above can be a target. Alternatively, fluids and individuals may be a target assuming that they are composed of a plurality of particles. The simulation with the particle simulation device 10 according to the present embodiment enables simulations of physical problems.

The functions of the particle simulation device 10 according to the present embodiment are improvements to the functions of the simulation described in Non-Patent Literature 1 above and Japanese Unexamined Patent Publication No. 2010-238030 (Patent Literature 1). Thus, the components of the particle simulation device 10 according to the present embodiment, except for the functions pertaining to the present invention, may be implemented by those described in Non-Patent Literature 1 and Patent Literature 1. Unless otherwise specified, the functions of the particle simulation device 10 are similar to those described in Patent Literature 1.

The particle simulation device 10 is configured as, for example, a computer including hardware such as a CPU (Central Processing Unit), a GPU (Graphics Processing Unit), a memory, a hard disk, and a display. These components operate under a program or the like to fulfill the functions as the particle simulation device 10 described later. The particle simulation device 10 operates effectively particularly in the case of using a device capable of parallel computing. The particle simulation device 10 may not necessarily include a GPU as a computing device and may be configured to include a CPU alone (scalar computer).

As shown in FIG. 1, the particle simulation device 10 is configured to include, as functional components, a particle information storage unit 11, a position information acquisition unit 12, a particle number setting unit 13, a pair setting unit 14, a reference information generation unit 15, a contact force calculation unit 16, a sum calculation unit 17, and a particle information calculation unit 18.

In the present embodiment, the work area that is an area in which particles move is a three-dimensional space and is divided (partitioned) into cubic cells with a preset size on each side as shown in FIGS. 2(*a*) and 2(*b*). The particle simulation device 10 divides the workspace into cells in advance before conducting the processing of simulation and grasps how the workspace is divided into cells in advance. The size of each side is, for example, Dmax×(1.0+α). Dmax is the largest value of the particle sizes of a plurality of particles targeted by the simulation. The parameter a is to adjust the frequency of updating a contact candidate list described later. For example, α=0.2. Alternatively, the size of each side may have a value greater than the cut-off length described later. Each cell in the work area is given a cell number for specifying the cell. Cell numbers are assigned in order, for example, according to the positions of cells in the workspace.

The particle information storage unit 11 is means for storing particle information for each of a plurality of particles in the work area. The particle information includes information indicating the coordinates of each particle, the velocity of each particle, and the particle radius. The coordinates of each particle are three-dimensional coordinates indicating the position of the particle in the workspace. The velocity of each particle includes translational velocity and rotational velocity. As for the coordinates of each particle and the velocity of each particle, the information at the start of simulation (initial information) is input to the particle information storage unit 11 in advance, for example, by the user of the particle simulation device 10, and the information during simulation is updated by the particle information calculation unit 18 described later. The particle radius is input to the particle information storage unit 11 in advance, for example, by the user of the particle simulation device 10. The particle information storage unit 11 may store information, other than the particle information, input in advance for use in simulation. Such information includes friction coefficient, elastic coefficient, viscous damping coefficient, and restitution coefficient.

The position information acquisition unit 12 is position information acquisition means for acquiring position information indicating the position of the particle, for each of a plurality of particles. The position information acquisition unit 12 acquires a cell number that is information indicating the cell in which the particle is positioned, as position information, for each of a plurality of particles. Specifically, the position information acquisition unit 12 acquires particle information at the present time (present step) of each particle that is stored in the particle information storage unit 11. The position information acquisition unit 12 determines which cell includes the coordinates of each particle indicated by the acquired particle information, and sets the cell number of the cell including the coordinates as position information of the particle of interest. The position information acquisition unit 12 outputs the acquired position information of the particle to the particle number setting unit 13 and the pair setting unit 14. The position information acquisition unit 12 also outputs the acquired particle information to the contact force calculation unit 16.

The acquisition of position information by the position information acquisition unit 12 and the processing based on the acquisition of position information may not be performed at each time but may be performed when the setting (updating) of particle pairs by the pair setting unit 14 described later is necessary. The position information acquisition unit 12 therefore may determine whether pairs are to be set (updated). This determination is performed, for example, as follows. For each particle, the cumulative distance of movement is calculated based on the coordinates of the particle at each time until the present time, and it is determined whether the cumulative distance of movement is greater than $r\alpha$, where r is the radius of the particle. If it is determined that the cumulative distance of movement is greater than $r\alpha$ in any one of the particles, it is determined that pairs are to be set (updated). The cumulative distance of movement is initialized when pairs are set (updated). Pairs are set at the initial time without performing the determination above.

When it is determined that the setting (updating) of pairs is necessary, the position information acquisition unit 12 outputs the acquired position information of the particle to the particle number setting unit 13 and the pair setting unit 14 to allow the processing of setting (updating) pairs. When it is determined that the setting (updating) of pairs is not necessary, the position information acquisition unit 12 may notify the contact force calculation unit 16 to that effect, and the processing by the contact force calculation unit 16 may be performed without setting (updating) pairs at this time.

Figure 2A:
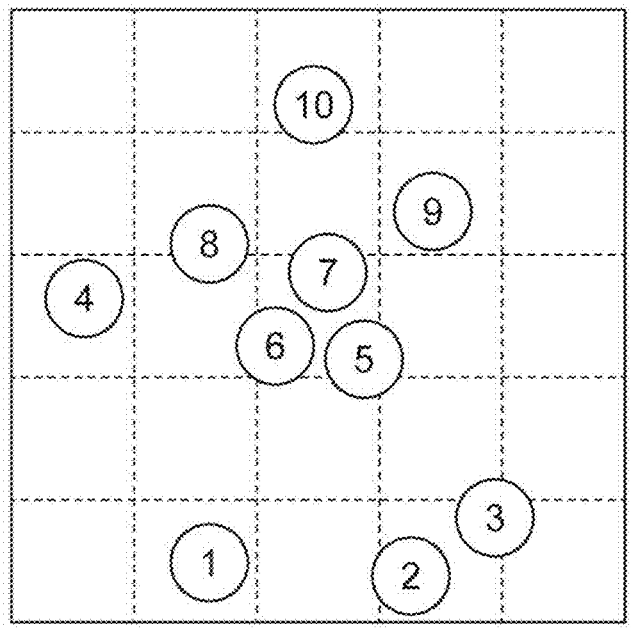
FIGS. 2(a) and 2(b) are diagrams showing a work area, particles included in the work area, and pairs formed with the particles in the present embodiment.

The particle number setting unit 13 is particle number setting means for setting a sortable particle number (particle index) for each of a plurality of particles. The particle number setting unit 13 sets a sortable particle number for each of a plurality of particles, based on the position information acquired by the position information acquisition unit 12. The particle number setting unit 13 arranges the particles according to the position information (in the order of cell numbers of cells to which the particles belong) and sets (reassigns) particle numbers in the order of position information. As particle numbers, for example, integers in ascending order starting from 1 are set. Through this setting of particle numbers, for example, as shown in FIG. 2(a), the particle numbers (in the example in FIG. 2(a), 1 to 10) ordered in accordance with the positions of particles are set for the particles. It is noted that the particle information is set such that the particle information stored in the particle information storage unit 11 can be acquired by a particle number, as illustrated in Patent Literature 1. The particle number setting unit 13 outputs the set particle numbers to the pair setting unit 14.

The pair setting unit 14 is pair setting means for selecting a pair of particles neighboring to each other based on the position information acquired by the position information acquisition unit 12, and setting a pair number (pair index) for the selected pair based on the particle number of one of particles of the selected pair that is set by the particle number setting unit 13. The particles neighboring to each other refer to two particles that may possibly be in contact with each other.

In the present embodiment, (it is assumed that) the upper triangular section of an interaction matrix U shown in FIG. 3(a) is configured. Here, i and j each are a particle number. The interaction matrix U is a matrix $U_{i,j}=1$ when the particle i and the particle j form a pair of neighboring particles, or $U_{i,j}=0$ when the particle i and the particle j do not form a pair of neighboring particles.

The pair setting unit 14 stores the largest value and the smallest value of particle numbers belonging to a cell into the memory of the particle simulation device 10 for each cell, based on the information input from the position information acquisition unit 12 and the particle number setting unit 13. The pair setting unit 14 sets particles belonging to the same cell or adjacent cells (for example, a total of 27 cells in the case of three-dimensional cells as in the present embodiment) as a pair of neighboring particles.

The adjacent relation of cells is stored in advance in the pair setting unit 14. The pair setting unit 14 refers to the thus stored largest value and smallest value of particle numbers of particles belonging to a cell and, for each particle, determines a particle to be paired from among particles having particle numbers set greater than the particle number of the particle of interest. For each particle, the pair setting unit 14 determines a particle having a particle number set greater than that of the particle of interest, as a particle to be paired, from among the particles belonging to the cell that the particle of interest belongs to and particles belonging to cells adjacent to the cell. It is noted that since particle numbers are assigned in the order of cell numbers of the cells that particles belong to, it is unnecessary to refer to a cell that includes only particles having smaller particle numbers than the particle number of the particle of interest. It is therefore only necessary to search 14 adjacent cells that include a particle j where i>j, for a particle i.

Here, whether particles are to be paired may be determined based on the particle center-to-center distance, rather than simply pairing particles belonging to adjacent cells. For example, it is determined whether the particle center-to-center distance is equal to or smaller than $(r_i+r_j)(1.0+\alpha)$, and a pair may be formed only when the condition above is satisfied. Here, $r_i$ and $r_j$ are the respective particle radii of the particles i and j.

Since the interaction matrix U shown in FIG. 3(a) requires much space on the memory, the pair setting unit 14 generates an array $U^{(1)}$ shown in FIG. 3(b) in which, for each particle number i of particles, the particle numbers of particles that have particle numbers greater than the particle number of the particle of interest and are paired are stored. The pair setting unit 14 also calculates, for each particle number i of the particles, the number of particles $n_{i<j}$ (the number of elements for each i in the array $U^{(1)}$) that have particle numbers greater than the particle number of the particle of interest and are paired, from $U^{(1)}$, as shown in FIG. 3(b).

Figure 2B:
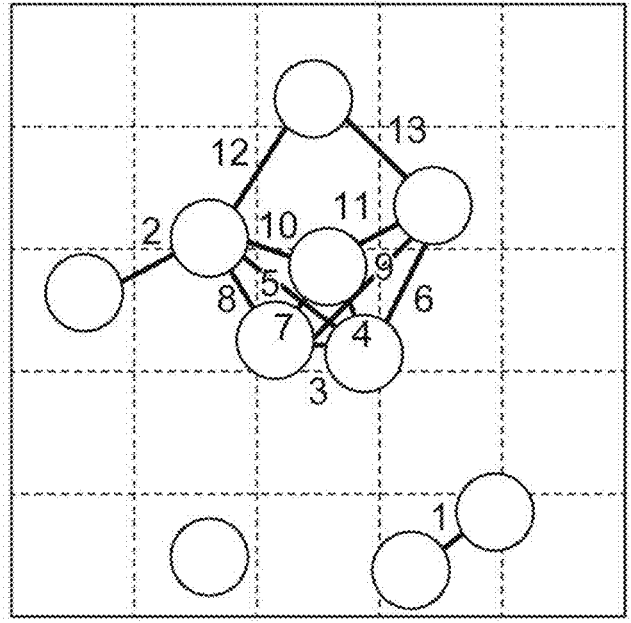

The pair setting unit 14 sets a pair number for the pair of particles set as described above. The pair setting unit 14 sets pair numbers in the ascending order of the smaller particle number of two particle numbers of a pair. As pair numbers, for example, integers in ascending order starting from 1 are set. If the smaller particle number of two particle numbers of a pair is identical, pair numbers are set in the ascending order of the larger particle number. In this way, a pair number is set based on the particle number of one of the particles of a pair (the smaller particle number of the particle numbers of two particles). Specifically, as illustrated in Patent Literature 1, the pair setting unit 14 sets a particle number, based on the prefix sum $s_{i<j}$ of the number of particles that have particle numbers greater than the particle number of the particle of interest and are paired for each particle number i. The pair numbers thus set are as shown in FIG. 2(b). The pair setting unit 14 generates a matrix $R^{(1)}$ shown in FIG. 3(b) in which the pair numbers of pairs formed with particles having a particle number j greater than the particle number i of the particle of interest are stored for each particle number i. The pair setting unit 14 outputs the generated $U^{(1)}$, $s_{i<j}$, and matrix $R^{(1)}$ to the reference information generation unit 15.

In addition, the pair setting unit 14 checks whether the present pair is the pair at the immediately preceding step, as illustrated in Patent Literature 1. As illustrated in Patent Literature 1, if the present pair is also the pair at the immediately preceding step, the pair setting unit 14 performs the processing of transferring the contact force of the pair at the immediately preceding step to the present pair.

The reference information generation unit 15 is reference information generation means for generating a matrix having the pair number set by the pair setting unit 14 and the particle numbers of particles of the pair as components of a row, sorting the order of a column of the matrix based on the particle number of another particle of the pair, and generating reference information for referring to the pair number of a pair including a particle by the particle number i of the particle, based on the sorted matrix. The reference information generation unit 15 sets the smaller particle number i of the particle numbers of particles of a pair as a component of one column of the matrix and sets the larger particle number j of the particle numbers of particles of the pair as a component of another column.

The reference information (pair list, pair index matrix) is referred to when the sum of contact force of each particle is calculated after the contact force generated between particles is calculated for each pair. The reference information for referring to the pair number of the pair with the particle j having a particle number (i<j) greater than the particle number i of the particle of interest is the matrix $R^{(1)}$ generated by the pair setting unit 14. The reference information generation unit 15 generates a matrix $R^{(2)}$ that is reference information for referring to the pair number of the pair with the particle j having a particle number (i>j) smaller than the particle number i of the particle of interest. $R^{(2)}$ is a matrix in which the pair number of the pair with a particle having a particle number smaller than the particle number of interest is stored for each particle number i.

The reference information generation unit 15 generates a matrix $T^{(1)}$ (triplet) having three columns as shown in FIG. 3(c), from $U^{(1)}$ and $R^{(1)}$ input from the pair setting unit 14. The first column is a pair number p. The second column and the third column are particle numbers of particles of the pair indicated by the pair number in the first column. The second column is the smaller particle number i of the particle numbers, and the third column is the larger particle number j. The reference information generation unit 15 generates a matrix $T^{(1)}$ by arranging the elements in rows such that the pair numbers p and the particle numbers i (one of the particle numbers) are in ascending order.

Subsequently, the reference information generation unit 15 sorts the rows (rearranges the rows) of the matrix $T^{(1)}$ such that the particle numbers j in the third column (the other particle numbers) are in ascending order to generate a matrix $T^{(2)}$ shown in FIG. 3(c). The reference information generation unit 15 counts the number of elements for each particle number j in the third column of the matrix $T^{(2)}$ to calculate $n_{i>j}$ shown in FIG. 3(d) (here, i in the index "i>j" of $n_{i>j}$ corresponds to the particle number j in the third column of the matrix $T^{(2)}$). For example, there is one row with j=3 in the particle numbers j in the third column of the matrix $T^{(2)}$, and then when i=3, $n_{i>j}$ is 1. There are three rows with j=9, and then when i=9, $n_{i>j}$ is 3. Here, $n_{i>j}$ is the number of particles that have particle numbers smaller than the particle number of the particle of interest and are paired for each particle number i of particles. In the approach in Non-Patent Literature 1, $n_{i>j}$ is also calculated but obtained by searching 27 adjacent cells in the approach in Non-Patent Literature 1.

Subsequently, the reference information generation unit 15 calculates the prefix sum $s_{i>j}(i)=\Sigma^i n_{i>j}(k)$ from $n_{i>j}$. Here, k is a variable (varied in the sum calculation) indicating a particle number. The reference information generation unit 15 generates the matrix $R^{(2)}$ shown in FIG. 3(d) from the matrix $T^{(2)}$, $n_{i>j}$, and $s_{i>j}(i)$. Specifically, the reference information generation unit 15 sets the pair numbers p of the $s_{i>j}(i-1)+1, \ldots, s_{i>j}(i-1)+n_{i>j}$-th rows in the first column of $T^{(2)}$, as the elements of the i-th (particle number i) row of the matrix $R^{(2)}$. As shown in FIG. 3(d), the number of i-th (particle number i) elements of the matrix $R^{(2)}$ is $n_{i>j}$.

The generation of the matrix $R^{(2)}$ by the reference information generation unit 15 can be implemented by the algorithm shown below.

[Math 1]

Require: $U^{(1)}$, $R^{(1)}$, $s_{i<j}$
for i = 1 to N do
   for j = 1 to $s_{i<j}(i)$ do
      $T_{j+s_{i<j}(i-1),1}^{(1)} \Leftarrow R_{i,j}^{(1)}$
      $T_{j+s_{i<j}(i-1),2}^{(1)} \Leftarrow i$
      $T_{j+s_{i<j}(i-1),3}^{(1)} \Leftarrow j$
   end for
end for
$T^{(2)} \Leftarrow$ Sort $T^{(1)}$ by $T_{,3}^{(1)}$
$s_{i>j}(0) = 0$
for i = 1 to N do
   $n_{i>j}(i) \Leftarrow$ Count number of i in $T_{,3}^{(2)}$
   $s_{i>j}(i) \Leftarrow s_{i>j}(i-1) + n_{i>j}(i)$
end for
for i = 1 to N do
   for j = 1 to $n_{i>j}(i)$ do
      $R_{i,j}^{(2)} \Leftarrow T_{s_{i<j}(i-1)+j,1}^{(2)}$
   end for
end for The reference information generation unit 15 outputs the generated reference information, $R^{(1)}$ and $R^{(2)}$, to the sum calculation unit 17. The reference information generation unit 15 also outputs information (for example, the matrix $T^{(1)}$) that can specify the correspondence between the pair number p and the particle numbers i and j of the particles of the pair indicated by the pair number p, to the contact force calculation unit 16.

The contact force calculation unit 16 is interaction force calculation means for performing a contact determination (interaction determination) between particles related to each of the pairs selected by the pair setting unit 14 and calculating the contact force between particles determined to be in contact (interact) with each other. The contact force calculation unit 16 specifies the correspondence between the pair number p of the pair selected by the pair setting unit 14 and the particle numbers i and j of the particles of the pair indicated by the pair number p, from the information input from the reference information generation unit 15.

The contact force calculation unit 16 inputs the particle information of particles of a pair that is stored in the particle information storage unit 11, from the position information acquisition unit 12. The contact force calculation unit 16 may also acquire a parameter required for calculation of the contact force that is stored in the particle information storage unit 11, and use the acquired parameter in calculation of the contact force. The contact force calculation unit 16 performs a contact determination between particles by calculating the particle-to-particle distance (or the particle center-to-center distance) based on the particle information and determining whether the calculated particle-to-particle distance is smaller than a threshold (cut-off length) stored in advance in the contact force calculation unit 16. When the particle-to-particle distance is smaller than the threshold, it is determined that the particles are in contact with each other.

When it is determined that the particles are in contact with each other, the contact force calculation unit 16 calculates the contact force for the pair. In this calculation of the contact force, each of the translational component and the rotational component of the contact force is calculated. The contact force is calculated based on the Voigt model as described in Patent Literature 1. When it is determined that the particles are not in contact with each other, the contact force calculation unit 16 sets the contact force to zero for the pair.

The contact force acting between particles is symmetric between the particles. That is, the relation of $F_{i,j}=-F_{j,i}$ holds, where $F_{i,j}$ is the contact force to which the particle having a particle number i is subjected from the particle having a particle number j, and $F_{j,i}$ is the contact force to which the particle having a particle number j is subjected from the particle having a particle number i. Then, the contact force $F_p$ to be calculated for each pair p can be written as $F_p = \sigma^p_{i,j} F_{i,j}$, where $\sigma^p_{i,j}$ is a projection operator to the pair <i,j> and has an inverse. Specifically, for example, the contact force calculation unit 16 calculates the contact force $F_p$ to be calculated for the pair p, as the contact force to which the particle having a smaller particle number i is subjected from the particle having a larger particle number j. The contact force calculation unit 16 stores the calculated contact force $F_p$ in an array associated with the pair number p, as described in Patent Literature 1. This information is referred to by the sum calculation unit 17.

For acceleration of the simulation, as described in Patent Literature 1, the contact determination and the calculation of the contact force by the contact force calculation unit 16 are performed by threading the pair numbers (in Patent Literature 1, contact candidate pair list numbers).

The sum calculation unit 17 is sum calculation means for calculating the sum of contact forces for each particle from the contact force calculated by the contact force calculation unit 16, based on the reference information generated by the reference information generation unit 15. The sum $F_i$ of particle contact forces generated in each particle having a particle number i can be calculated by the formula below.

$$F_i = \sum_j \tilde{\sigma}^p_{i,j} F_p \qquad \text{[Math 2]}$$

In the formula above, $\sigma^p_{i,j}$ with a tilde is the inverse of $\sigma^p_{i,j}$. When $F_p$ is defined as the contact force to which the particle having a smaller particle number i is subjected from the particle having a larger particle number j as described above, the inverse of $\sigma^p_{i,j}$ is 1 (the forward sign of $F_p$) if i<j, and is −1 (the opposite sign of $F_p$) if j<i.

Specifically, the sum calculation unit 17 refers to the reference information $R^{(1)}$, $R^{(2)}$ generated by the reference information generation unit 15 to specify the pair of particles to be targeted in calculation of the sum. Subsequently, the sum calculation unit 17 acquires (reads out) the contact force $F_p$ calculated by the contact force calculation unit 16 for the specified pair. The sum calculation unit 17 calculates the sum $F_i$ of contact forces generated in the particle based on the formula above, from the acquired contact force. The value of the inverse of $\sigma^p_{i,j}$ is specified by whether a pair is specified from either the reference information $R^{(1)}$ or $R^{(2)}$. When a pair is specified from the reference information $R^{(1)}$, the inverse of $\sigma^p_{i,j}$ is 1, given that i<j. When a pair is specified from the reference information $R^{(2)}$, the inverse of $\sigma^p_{i,j}$ is −1, given that i>j. The sum calculation unit 17 outputs information indicating the calculated sum $F_i$ of contact forces of each particle to the particle information calculation unit 18.

The particle information calculation unit 18 is particle information calculation means for calculating the position and velocity of a particle at the next time (step), based on the sum of contact forces for each particle that is calculated by the sum calculation unit 17. Specifically, for each particle, the particle information stored in the particle information storage unit 11 is acquired, and the coordinates and velocity at the next time (step) are calculated from the coordinates and velocity at present time (present step) indicated by the particle information and the sum of contact forces. This calculation can be performed, for example, using the leap-flog method as illustrated in Patent Literature 1. The particle information calculation unit 18 updates the particle information stored in the particle information storage unit 11 for each particle with the calculated position and velocity of the particle at the next time (step). When the particle information calculation unit 18 makes updates for all of the particles, the processing at the next time (step) is performed.

In the particle simulation device 10, every time the computation at one time (step) is completed, it is determined whether the termination condition of simulation is satisfied. For example, when the computation is finished a preset number of times (time (step)), it is determined that the termination condition is satisfied. If it is determined that the termination condition is satisfied, the simulation is terminated in the particle simulation device 10. In this case, for example, the computation result is output to a display device or other devices. If it is determined that the termination condition is not satisfied, the computation at the next time (step) is repeatedly performed. The configuration of the particle simulation device 10 is as described above.

Figure 4:
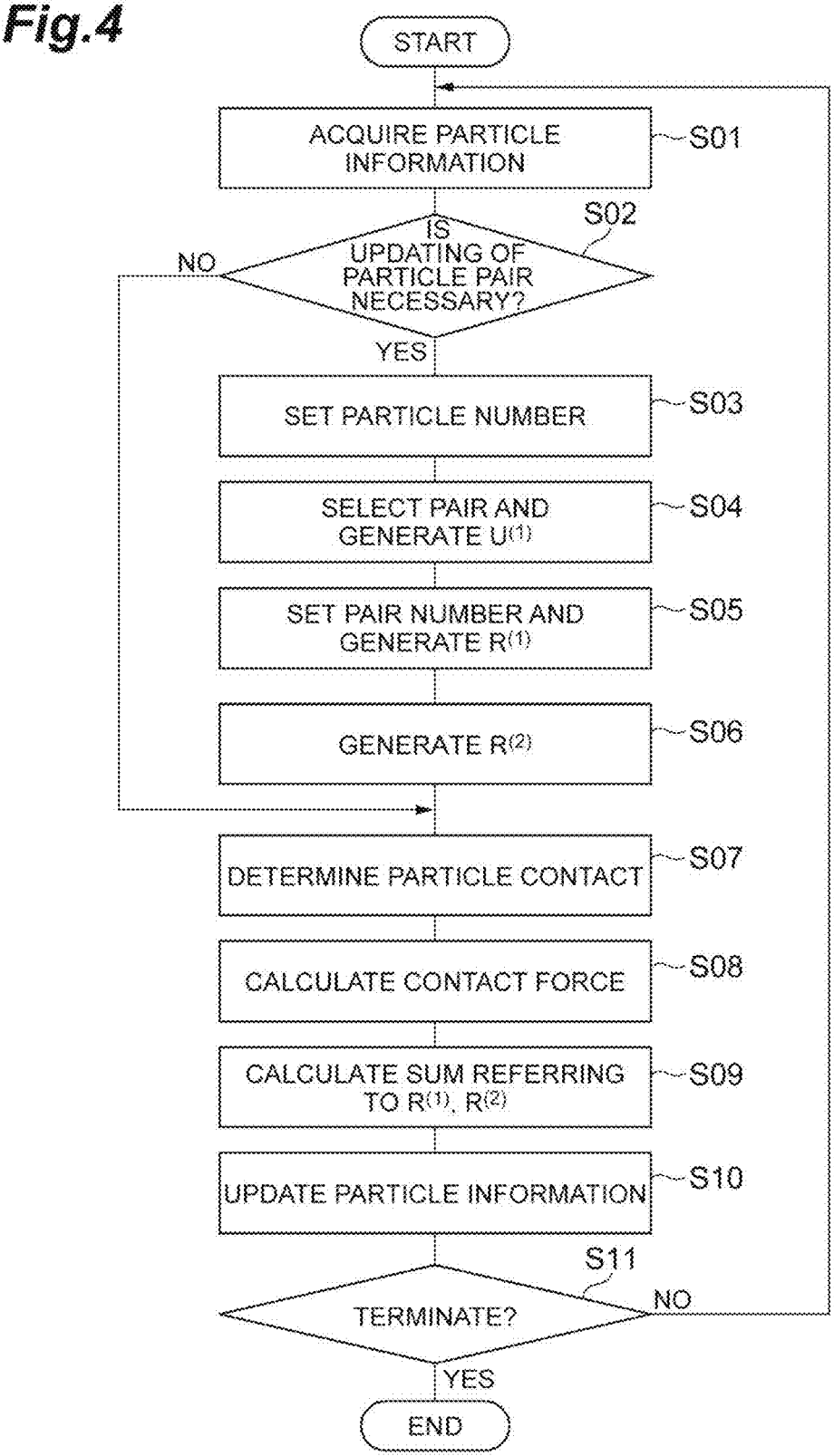
FIG. 4 is a flowchart showing the entire processing (particle simulation method) performed in the particle simulation device according to an embodiment of the present invention.
Figure 5:
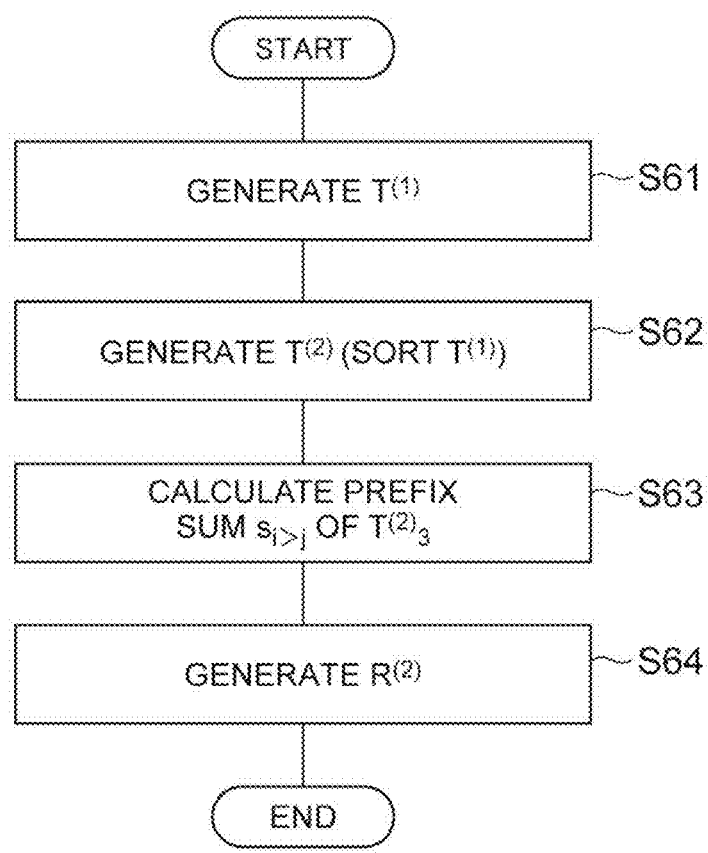
FIG. 5 is a flowchart showing a process of generating $R^{(2)}$ that is reference information.

Referring now to the flowcharts in FIG. 4 and FIG. 5, the processing executed in the particle simulation device 10 (particle simulation method) will be described, which is a method of operating the particle simulation device 10 according to the present embodiment. The entire processing of the present processing is described with reference to FIG. 4, and the generation of the reference information $R^{(2)}$ is described with reference to FIG. 5. The present processing is started, for example, by the user of the particle simulation device 10 performing the operation of starting analysis for the particle simulation device 10.

In the particle simulation device 10, the position information acquisition unit 12 acquires the particle information at present time of each particle that is stored in the particle information storage unit 11 (S01, position information acquisition step). The cell number of the cell that includes the coordinates of a particle indicated by the particle information is set as position information of the particle. Subsequently, the position information acquisition unit 12 determines whether the setting (updating) of a pair is necessary (S02). In the processing at the initial time, this determination is not made and the setting of a pair is always performed.

If it is determined that the setting (updating) of a pair is necessary (YES in S02), the position information of the particle is output from the position information acquisition unit 12 to the particle number setting unit 13 and the pair setting unit 14. In addition, the particle information is output from the position information acquisition unit 12 to the contact force calculation unit 16. Subsequently, the particle number setting unit 13 sets (reassigns, in the setting for the second and subsequent times) the particle number based on the position information for each particle (S03, particle number setting step). The set particle number is output from the particle number setting unit 13 to the pair setting unit 14.

Subsequently, the pair setting unit 14 determines a particle to be paired with each particle and generates an array $U^{(1)}$ in which the particle number of the particle that has a particle number greater than the particle number of the particle of interest and is paired is stored for each particle number i of particles (S04, pair setting step). Subsequently, the pair setting unit 14 sets a pair number for a pair of particles and generates a matrix $R^{(1)}$ in which the pair number of the pair with a particle having a particle number greater than the particle number of the particle of interest is stored for each particle number i (S05, pair setting step). The information generated by the pair setting unit 14 is output to the reference information generation unit 15.

Subsequently, the reference information generation unit 15 generates a matrix $R^{(2)}$ that is reference information for referring to the pair number of the pair with a particle j having a particle number (i>j) smaller than the particle number i of the particle of interest (S06, reference information generation step).

The processing of generating the matrix $R^{(2)}$ by the reference information generation unit 15 will be described in more details with reference to the flowchart in FIG. 5. In the present processing, a matrix $T^{(1)}$ is generated from $U^{(1)}$ and $R^{(1)}$ input from the pair setting unit 14 (S61). Subsequently, the rows of the matrix $T^{(1)}$ are sorted based on the particle numbers j in the third column of the matrix $T^{(1)}$ to generate a matrix $T^{(2)}$ (S62). Subsequently, the number of elements $n_{i>j}$ for each particle number j in the third column of the matrix $T^{(2)}$ and the prefix sum $s_{i>j}$ of the third column $(T^{(2)}_3)$ of the matrix $T^{(2)}$ are calculated (S63). Subsequently, a matrix $R^{(2)}$ is generated from the matrix $T^{(2)}$, $n_{i>j}$, and $s_{i>j}(i)$ (S64). The processing of generating the matrix $R^{(2)}$ is as described above.

Returning to FIG. 4, subsequently, the generated reference information $R^{(1)}$ and $R^{(2)}$ are output from the reference information generation unit 15 to the sum calculation unit 17. In addition, information (for example, matrix $T^{(1)}$) that can specify the correspondence between the pair number p and the particle numbers i, j of particles of the pair indicated by the pair number p is output from the reference information generation unit 15 to the contact force calculation unit 16.

If it is determined that the setting (updating) of a pair is not necessary in step S02 (NO in S02), or after S06, then the contact force calculation unit 16 performs a contact determination between particles of a pair, for each pair (S07, interaction force calculation step). If the pair is not to be updated, information of the pair at the immediately preceding time (step) is used in the present processing. Subsequently, the contact force calculation unit 16 calculates contact force for the pair having particles determined to be in contact with each other (S08, interaction force calculation step). For the pair having particles determined not in contact with each other, the contact force is set to zero. The calculated contact force is stored in an array associated with the pair number p and is referred to by the sum calculation unit 17.

Subsequently, the sum calculation unit 17 refers to the reference information $R^{(1)}$, $R^{(2)}$ generated by the reference information generation unit 15 to calculate the sum of contact forces for each particle from the contact force calculated by the contact force calculation unit 16 (S09, sum calculation step). Information indicating the calculated sum $F_i$ of contact forces for each particle is output from the sum calculation unit 17 to the particle information calculation unit 18.

Subsequently, the particle information calculation unit 18 calculates the position and velocity of the particle at the next time (step), based on the sum of contact forces for each particle that is calculated by the sum calculation unit 17 (S10, particle information calculation step). Subsequently, the particle information stored in the particle information storage unit 11 is updated for each particle with the position and velocity calculated by the particle information calculation unit 18.

Subsequently, in the particle simulation device 10, it is determined whether the termination condition of simulation is satisfied (S11). If it is determined that the termination condition is satisfied (YES in S11), the processing (simulation) ends. If it is determined that the termination condition is not satisfied (NO in S11), the time (step) is advanced by one, and the processing described above (S01 to S11) at the next time (step) is performed. The processing performed in the particle simulation device 10 according to the present embodiment is as described above.

The simulation method described in Non-Patent Literature 1 compared with the present invention will now be described. Also in the method described in Non-Patent Literature 1, the work area is divided into cells as in the present embodiment, and the particle number corresponding to the position of each particle is set for each particle.

In the method described in Non-Patent Literature 1, (it is assumed that) an interaction matrix U shown in FIG. 6(a) is configured. This matrix U corresponds to the interaction matrix U in the present embodiment shown in FIG. 3(a). In the method described in Non-Patent Literature 1, however, the interaction matrix U additionally includes the lower triangular section, unlike the present embodiment.

In the method described in Non-Patent Literature 1, considering the memory space to store, arrays $U^{(1)}$ and $U^{(2)}$ shown in FIG. 6(b) are generated as the interaction matrix U. The array $U^{(1)}$ is the same as $U^{(1)}$ in the present embodiment. The array $U^{(2)}$ is an array in which the particle numbers of particles that have particle numbers smaller than the particle number of the particle of interest and are paired are stored for each particle number i of particles. These matrices are configured by searching 27 adjacent cells. At the same time, the number of particles $n_{i<j}$ that have particle numbers greater than the particle number of the particle of interest and are paired (the number of elements for each i in the array $U^{(1)}$) and the number of particles $n_{i>j}$ that have particle numbers smaller than the particle number of the particle of interest and are paired (the number of elements for each i in the array $U^{(2)}$) are calculated for each particle number i of particles.

In the method described in Non-Patent Literature 1, subsequently, for example, (it is assumed that) a pair number is set for a pair between particles as shown in FIG. 6(c) by assigning a sequential number to one element of the interaction matrix U shown in FIG. 6(a). However, U as mentioned above is actually not generated but a matrix $R^{(1)}$ shown in FIG. 6(d) is generated from the array $U^{(1)}$ and the prefix sum, in the same manner as in the present embodiment. The matrix $R^{(1)}$ is the same as $R^{(1)}$ in the present embodiment.

Subsequently, $R^{(2)}$ is generated by the i-th thread searching the elements of $R^{(1)}_{i,j}$ corresponding to $R^{(2)}$. Here, the i-th thread reads out the values of $U^{(1)}_{i,j}$ and searches the $U^{(1)}_{i,j}$-th row of $U^{(2)}$. When the element having a value of i is found, the thread sets the element of $R^{(1)}_{i,j}$ as the element of $R^{(2)}$. This process is repeated for j, and $R^{(2)}$ is generated.

More specifically, the generation of the matrix $R^{(2)}$ in Non-Patent Literature 1 can be implemented by the algorithm shown below. The matrix $R^{(2)}$ is the same as $R^{(2)}$ in the present embodiment.

[Math 3]

Require: $U^{(1)}$, $U^{(2)}$, $R^{(1)}$, $s_{i<j}$, $n_{i>j}$
for i = 1 to N do
   for j = $s_{i<j}$(i − 1) + 1 to $s_{i<j}$(i) do
      for k = 1 to $n_{i>j}(U_{i,j}^{(1)})$ do
         if $U_{j,k}^{(2)} = i$ then
            $R_{j,k}^{(2)} \Leftarrow R_{i,j}^{(1)}$
        end if
      end for
   end for
end for In the method described in Non-Patent Literature 1, $R^{(1)}$ and $R^{(2)}$ are used to perform a particle simulation in the same manner as in the present embodiment.

Figure 7A:
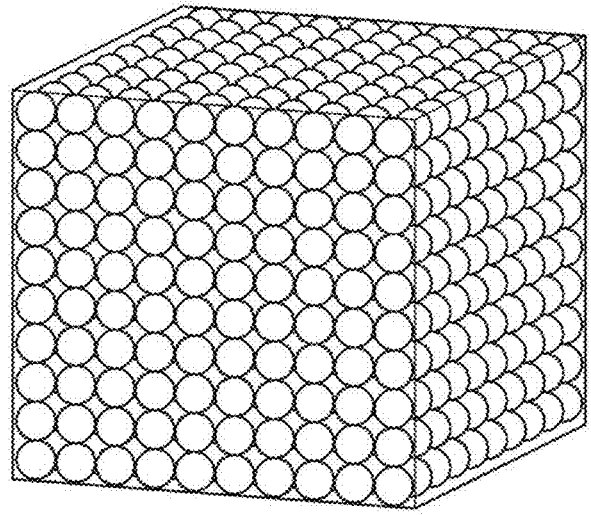
FIGS. 7(a) and 7(b) illustrate a model used in a performance test in the method described in Non-Patent Literature 1 and the results of the performance test.

The result of a performance test conducted for the method described in Non-Patent Literature 1 will now be illustrated. In this performance test, particles were arranged evenly in a simulation box serving as a work area, and a pair index matrix, which is $R^{(1)}$, $R^{(2)}$, was obtained. Here, the simulation box was a three-dimensional space having a size of $L^3$, and particles were arranged evenly as shown in FIG. 7(a). The simulation box is divided into cubic cells with l=L/4 on each side. The cut-off length $r_c$ was set slightly smaller than l.

Figure 7B:
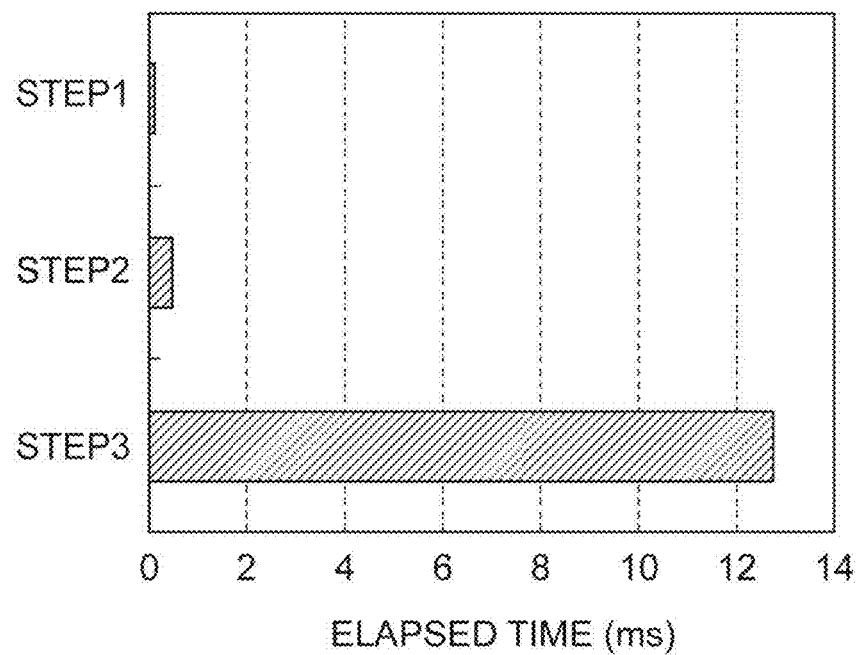

In this performance test, the processing is divided into three steps. Step 1 is cell division and sorting, Step 2 is construction of the upper triangular section of the pair index matrix, and Step 3 is construction of the lower triangular section of the pair index matrix. The results of the performance test are shown in FIG. 7(b). The graph in FIG. 7(b) shows the elapsed time taken to execute the computation for each step. As shown by this performance test, Step 3 requires more computation than the other steps.

As previously mentioned, at Step 3, the i-th thread searches the elements of $R^{(1)}_{i,j}$ corresponding to $R^{(2)}$. In this processing, the i-th thread searches one row of $U^{(2)}$, and this search is repeated for one row of $R^{(1)}$. That is, in the algorithm in the method described in Non-Patent Literature 1, the search is conducted with a double for-loop including if statement (condition determination). This causes problems including warp divergence to significantly reduce the calculation performance of the GPU. The simulation method described in Non-Patent Literature 1 is as described above.

Based on the simulation method described in Non-Patent Literature 1 above, the effects of the present embodiment will be described. As previously mentioned, in the method described in Non-Patent Literature 1, a number of trial-and-error processes are the cause of reduction in performance. By contrast, in the present embodiment, reference information is generated by using the sorted matrix without using a double for-loop. This eliminates the need for a number of trial-and-error processes. That is, the present embodiment can improve the computation efficiency. It is noted that the method using a pair list as in the present embodiment is a method that does not require atomic operations and enables parallel calculation of contact force.

As in the present embodiment, the column of the matrix $T^{(1)}$ having three columns for generating reference information $R^{(2)}$ may be the smaller particle number i of the particles numbers of particles of a pair, and the other column may be the larger particle number j of the particles numbers of particles of the pair. With this configuration, the reference information $R^{(2)}$ can be generated based on the matrix $T^{(2)}$ sorted appropriately and reliably. This enables the present invention to be carried out appropriately and reliably.

As in the present embodiment, a sortable particle number may be set for each of a plurality of particles, based on the position information. With this configuration, particle numbers can be assigned to particles appropriately and reliably. This enables the present invention to be carried out appropriately and reliably.

As in the present embodiment, the work area may be divided into cells to perform simulation. This configuration enables efficient and easy selection of a pair of neighboring particles and can further improve the computation efficiency.

Although in the present embodiment, contact force by contact between particles is used as interaction force acting on particles, the interaction in the present invention is not limited to contact. Any interaction that allows force (interaction force) to act between particles can be a target.

The results of a performance test according to the present embodiment will now be illustrated. In order to conduct the test, a static array of particle positions was prepared, from which calculation costs for constructing a pair index matrix were measured. The system was a three-dimensional simulation box having a size of $L^3$. In this simulation box, $N=10^3$ particles are arranged irregularly. The simulation box is divided into cubic cells having a length of l on each side. The cut-off length $r_c$ of interaction is set slightly smaller than l.

In the present performance test, several values are set for l. That is, the effect of the size of the interaction matrix is determined in performance. In the present performance test, a code (algorithm) pursuant to Non-Patent Literature 1 and a code (algorithm) pursuant to the present embodiment were implemented and compared with each other. The two codes are the same excluding their respective essential parts. The present code was implemented by CUDA and tested on TESLA C2075. The important operations in the present embodiment are sorting, counting, and prefix sum. In order to implement these operations, the existing Thrust library was used in implementation for sorting and prefix sum. The performance was measured in terms of the elapsed time taken to construct a pair index matrix.

Figure 8:
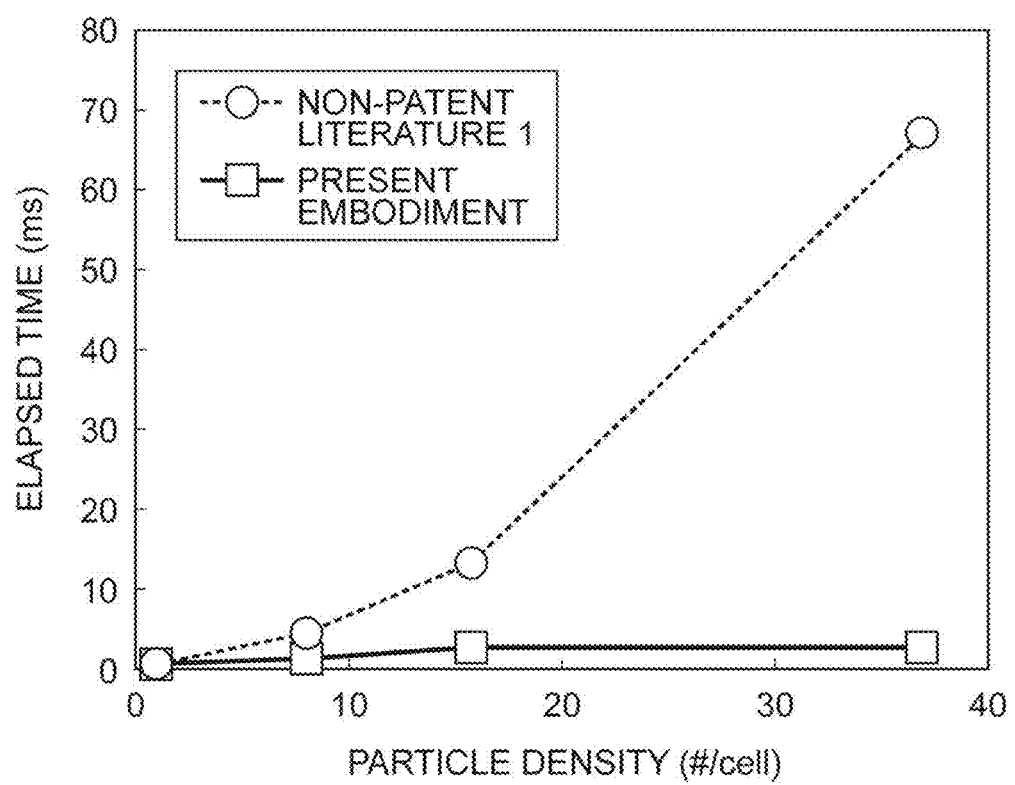
FIG. 8 is a graph showing the relation between the particle density and the elapsed time taken to generate a pair index matrix in a performance test in the present embodiment and the method described in Non-Patent Literature 1.

The measurement results of the two codes are shown in FIG. 8. FIG. 8 illustrates the relation between the particle density and the elapsed time taken to generate a pair index matrix. The elapsed time is a total time taken for cell division, sorting, and construction of the upper triangular section and the lower triangular section of a pair index matrix. As shown in FIG. 8, the performances of the two codes are similar when the particle density is small, but as the particle density increases, the performance in the present embodiment significantly increase. This result indicates that as the size of the matrix increases, the effect of improving performance in the present embodiment increases. The approach of the present invention uses the divide-and-conquer technique in which the effect increases as the object increases. When the particle density is 1, overhead of sorting occurs and thus the superiority in performance is slightly reversed.

Figure 9A:
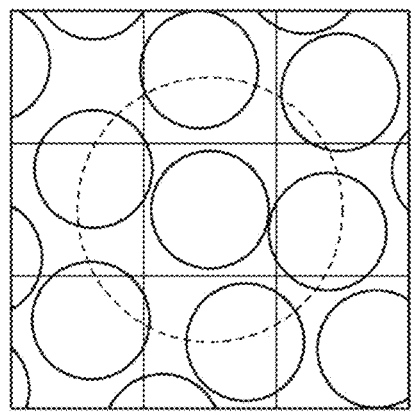
FIGS. 9(a) to 9(c) illustrate an example of particle density in a particle simulation.
Figure 9B:
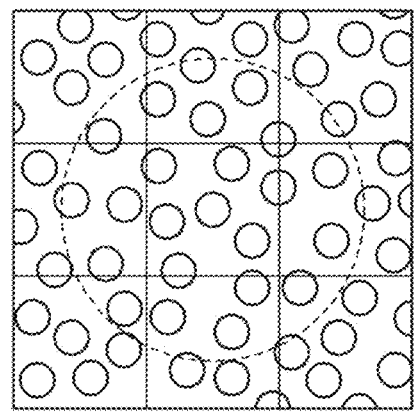
Figure 9C:
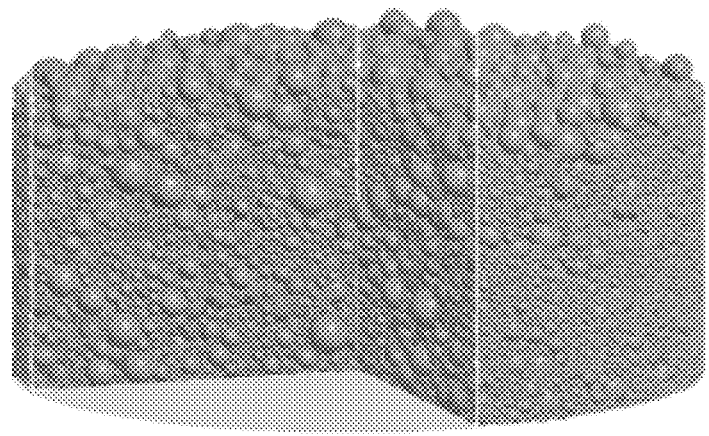

Improvement by the approach of the present invention can be achieved by understanding the types of simulation. FIGS. 9(a) to 9(c) show peculiar simulations supposed in DEM and SPH simulations. As shown in FIG. 9(a), in DEM, a particle interacts with another particle with strong contact force acting only around the shell, and therefore each cell includes a small number of particles. On the other hand, as shown in FIG. 9(b), the particle in SPH has a shell acting very flexibly and interacts with a number of other particles. For stable calculation, the cut-off radius of a particle in hydraulics may be set two to four times as large as the average particle-to-particle distance. The particle density supposed in SPH simulation is about ten to a few tens, and the algorithm of the present embodiment is very efficient in this range of density. Therefore, the present invention improves a particle system including many interaction pairs such as in SPH and MD rather than DEM.

The present invention is effective also in DEM when the radii of particles are widely distributed. As shown in FIG. 9(c), for example, in the studies of the Brazil nut problem, the size of the largest particle is a few times greater than the size of the smallest particle. When the largest radius is $r_{max}$ and the smallest radius is $r_{min}$, the particle density in a cell is as low as $(r_{max}/r_{min})^3$. This is because when a particle system having uniform cells is simulated, the cell size has to be set so as to accommodate the largest particle. The algorithm of the present embodiment is obviously efficient in this type of simulation.

Figures 10A, 10B:
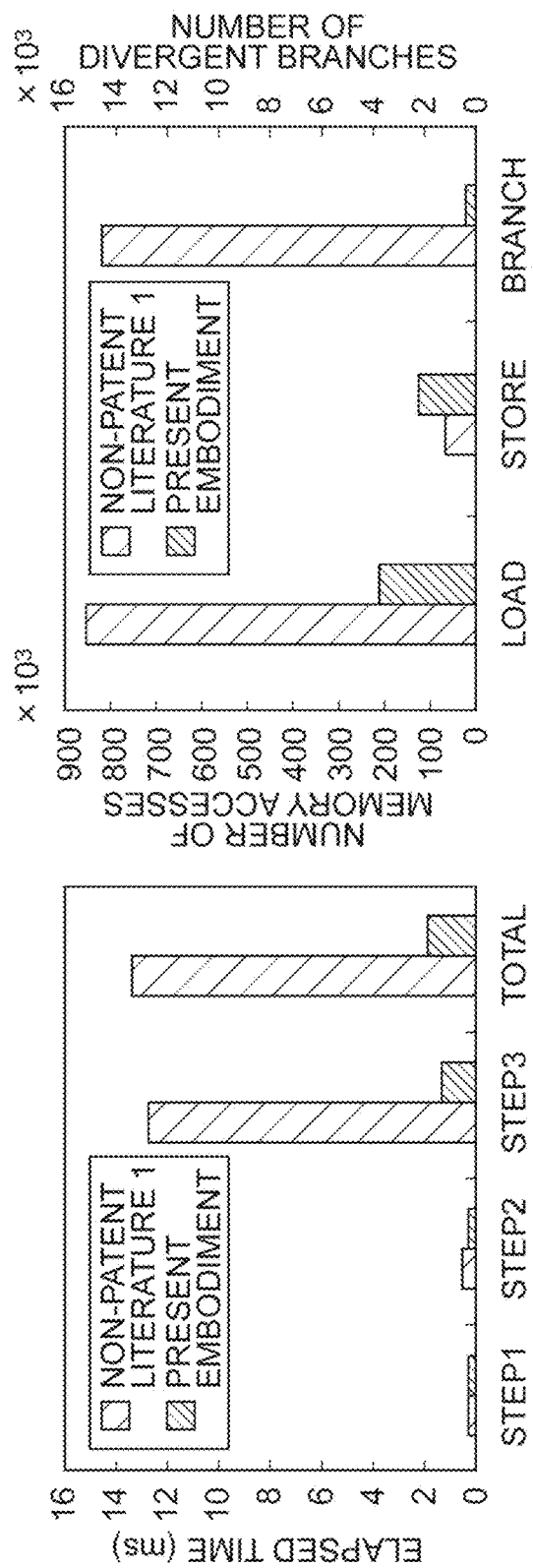
FIGS. 10(*a*) and 10(*b*) illustrate graphs showing the elapsed time for each step and the number of memory accesses in a performance test in the present embodiment and the method described in Non-Patent Literature 1.

The performance according to the present embodiment will be illustrated in more details. As typically supposed in SPH simulation, here, L/l=4. FIG. 10(a) shows the elapsed time in connection with the construction of a pair index matrix in the code pursuant to Non-Patent Literature 1 and the code pursuant to the present embodiment. In Step 2 and Step 3, the performance is improved. The performance improvement in Step 2 is achieved by reduction of the search range. The number of neighbor cells to be searched is 27 in the code pursuant to Non-Patent Literature 1, and 14 in the code pursuant to the present embodiment.

A significantly great improvement is achieved in Step 3. This is possibly attributable to a number of trial-and-error processes, which is supported by the profiling result shown in FIG. 10(b). FIG. 10(b) shows the number of load (memory read) and store (store) instructions and the number of branches (divergent branches) counted by a profiler. The number of memory read instructions in the entire processing is clearly reduced. The drastic reduction in number of branches indicates that the code pursuant to the present embodiment appropriately avoids warp divergence. As described above, the present embodiment is successful in accelerating construction of the pair index matrix.

The effectiveness of the present invention for the entire particle simulation was evaluated as follows. Specifically, SPH simulation was conducted, including construction of a pair list, computation of force, summing of force, and summation of equations of motion. The particles follow equations of motion, and in addition to contact force $f_{i,j}$ between particles, external force $f_{ext}$ acting on particles is taken into consideration for the particles. In the present simulation, it is assumed that the particles free fall under gravity. That is, $f_{ext}=\rho g$. Here, $\rho$ is the mass density calculated with SPH, and g is a gravitational acceleration vector. For the expression of stress and density in the Lagrangian form, the framework suggested by M. Muller, D. Charypar, M. Gross, Particle-based fluid simulation for interactive applications, in Proceedings of 2003 ACM SIGGRAPH Symposium, 2003, pp. 154-159, was used. The aforementioned framework is unsuitable for execution of fluid simulation but is convenient for evaluating improvement of algorithms because the framework is very simple.

Figure 11:
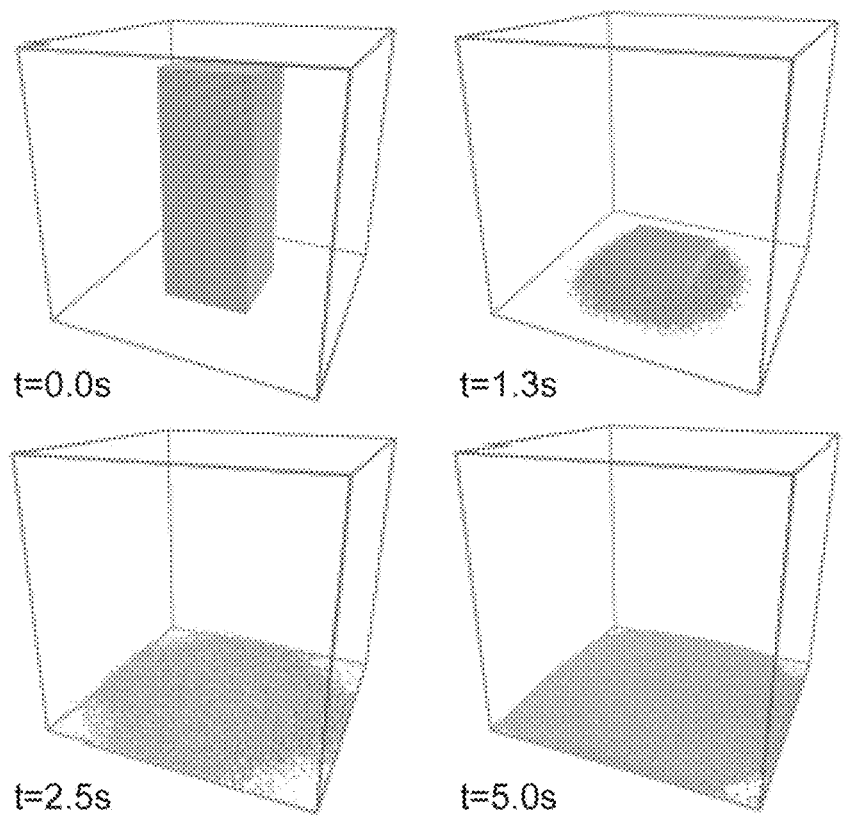
FIG. 11 illustrates the states (snap shots) of a model used in the performance test during execution of a simulation.

Let L=10 m, l=0.1 m, and the cut-off length r of a kernel function=0.08 m. As shown in FIG. 11, in the initial state, $N=10^6$ particles were arranged in a column shape, and the distance between particles was set to $r_c$ or greater. The equation of motion was discretized by the symplectic scheme, and the time interval $\Delta t=5.0\times 10^{-4}$ s was set. Iterations were performed until t=5.0 s.

The effective particle density $\rho^*$, which is one of the important indicators indicating the feature of the system, is defined by the formula below.

$$\rho^* = \frac{1}{14N} \sum_{k}^{N} n_{i<j}(k) \qquad \text{[Math 4]}$$

Figure 12A:
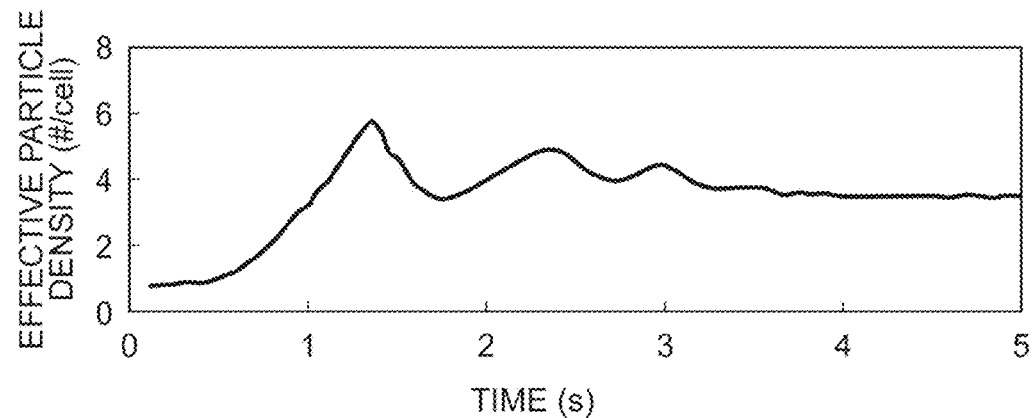
FIGS. 12(*a*) and 12(*b*) illustrate graphs showing the relations between the time (step) and the effective particle density and between the time (step) and the elapsed time taken to generate a pair index matrix in a performance test in the present embodiment and the method described in Non-Patent Literature 1.

In the present simulation, parameters such as the mass of particles were set such that the stable effective density was up to 3.5/cell. As shown in FIG. 12(a), the changing effective density during simulation was measured. As shown in FIG. 12(a), the effective density had the largest value when t was about 1.3, and the fluid was compressed almost due to gravity fall. The pair list was updated with $\max(\Delta x)>(1-r_c)/2$ when the largest cumulative distance of movement $\Delta x$ exceeds a critical value.

Figure 12B:
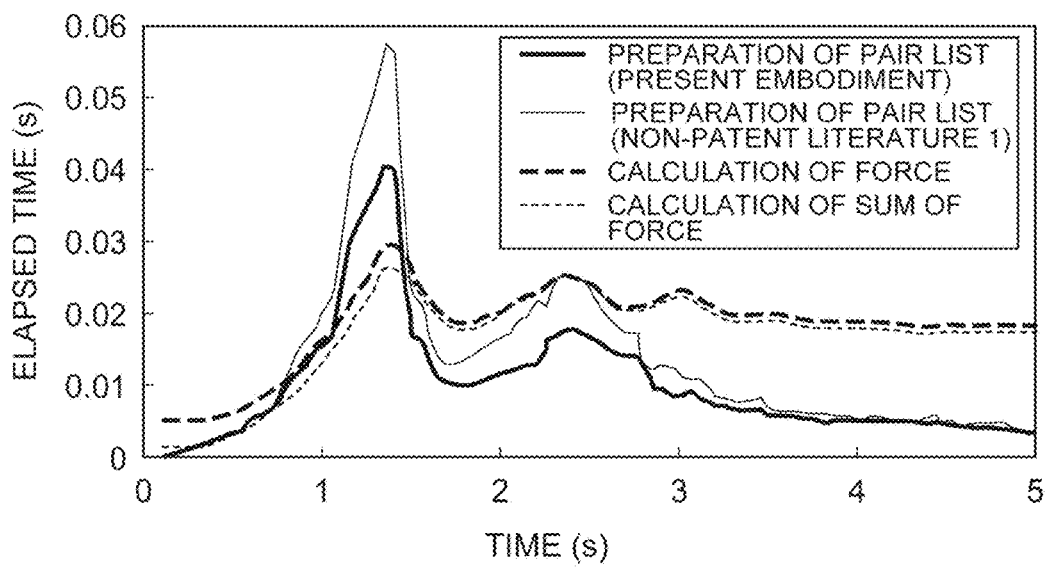

Furthermore, as shown in FIG. 12(b), the elapsed time taken to execute calculation, summing, and time summation of force was measured at each time (step). In the graph in FIG. 12(b), the elapsed time taken to construct a pair list is measured, and the moving average of 100 times (steps) is shown. In the graph in FIG. 12(b), when t having the largest value of effective density is about 1.3, it takes the longest time to construct a pair list, and the time taken to construct a pair list is shorter in the present embodiment than in the method described in Non-Patent Literature 1. In this way, the present embodiment particularly improves the performance particularly in compression of fluid through gravity shock.

Furthermore, the present embodiment enables frequent updating of the pair list of particles without a signification reduction in performance. The results described above indicate that the present embodiment can accelerate simulation including high compression through shock. This indicates that the present embodiment is efficient even when the simulation includes vigorous motion of particles such as turbulence. In this example, a somewhat small value ($\rho^*$ up to 3.5/cell) was selected for stable effective density. In order to perform a stable SPH simulation, a greater stable density should be taken. This is because a high density can avoid instability such as high pressure vibration. If a high stable density is used, the improvement of the present embodiment is more prominent. In this way, the present embodiment is effective in acceleration of a particle simulation.

Figure 13:
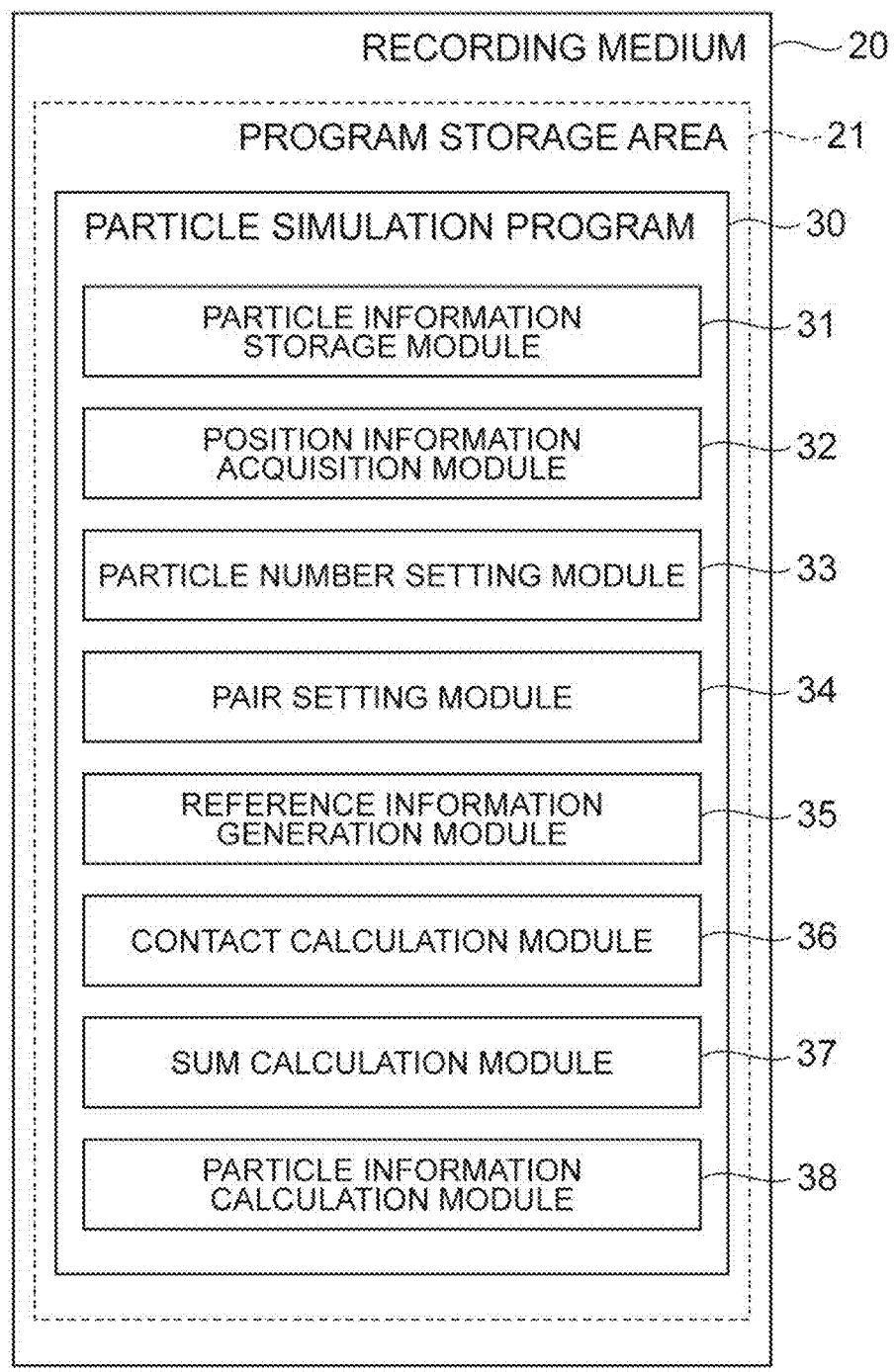
FIG. 13 is a diagram showing a configuration of a particle simulation program according to an embodiment of the present invention, with a recording medium.

A particle simulation program for causing a computer to execute the processing by the particle simulation device 10 as described above will now be described. As shown in FIG. 13, a particle simulation program 30 is stored in a program storage area 21 formed in a recording medium 20 inserted to a computer and accessed, or of a computer.

The particle simulation program 30 is configured to include a particle information storage module 31, a position information acquisition module 32, a particle number setting module 33, a pair setting module 34, a reference information generation module 35, a contact force calculation module 36, a sum calculation module 37, and a particle information calculation module 38. The functions implemented by executing the particle information storage module 31, the position information acquisition module 32, the particle number setting module 33, the pair setting module 34, the reference information generation module 35, the contact force calculation module 36, the sum calculation module 37, and the particle information calculation module 38 are similar to the particle information storage unit 11, the position information acquisition unit 12, the particle number setting unit 13, the pair setting unit 14, the reference information generation unit 15, the contact force calculation unit 16, the sum calculation unit 17, and the particle information calculation unit 18, respectively, of the particle simulation device 10 described above.

The particle simulation program 30 may be partially or entirely transmitted through a transmission medium such as a communication network and received by another equipment and recorded (including installation). The modules of the particle simulation program 30 may be installed not in a single computer but in any of a plurality of computers. In this case, a computer system including the computers performs the aforementioned processing of the particle simulation program 30.

INDUSTRIAL APPLICABILITY

Reference Signs List

10 . . . particle simulation device, 11 . . . particle information storage unit, 12 . . . position information acquisition unit, 13 . . . particle number setting unit, 14 . . . pair setting unit, 15 . . . reference information generation unit, 16 . . . contact force calculation unit, 17 . . . sum calculation unit, 18 . . . particle information calculation unit, 20 . . . recording medium, 21 . . . program storage area, 30 . . . particle simulation program, 31 . . . particle information storage module, 32 . . . position information acquisition module, 33 . . . particle number setting module, 34 . . . pair setting module, 35 . . . reference information generation module, 36 . . . contact force calculation module, 37 . . . sum calculation module, 38 . . . particle information calculation module.

The invention claimed is:

1. A particle simulation device configured to calculate position and velocity of a plurality of particles in a workspace based on interaction force with another particle and simulates behavior of the particles, the particle simulation device comprising:
   position information acquisition means for acquiring position information indicating a particle position, for each of the plurality of particles;
   particle number setting means for setting a sortable particle number for each of the plurality of particles;
   pair setting means for selecting a pair of particles neighboring to each other based on the position information acquired by the position information acquisition means, and setting a pair number for the pair based on the particle number of one of particles of the pair that is set by the particle number setting means;
   reference information generation means for generating a matrix having the pair number set by the pair setting means and the particle numbers of particles of the pair as components of a row, sorting order of a column of the matrix based on the particle number of another particle of the pair, and generating reference information for referring to the pair number of a pair including a particle by the particle number of the particle, based on the sorted matrix;
   interaction force calculation means for performing an interaction determination between particles related to each of pairs selected by the pair setting means and calculating interaction force between particles determined to interact;
   sum calculation means for calculating a sum of interaction forces for each particle, from the interaction force calculated by the interaction force calculation means, based on the reference information generated by the reference information generation means; and
   particle information calculation means for calculating position and velocity of a particle, based on the sum of interaction forces for each particle that is calculated by the sum calculation means.

2. The particle simulation device according to claim 1, wherein
   the reference information generation means sets a smaller particle number of the particle numbers of particles of the pair as a component in one column of the matrix and sets a larger particle number of the particle numbers of the particles of the pair as a component in another column.

3. The particle simulation device according to claim 1, wherein
   the particle number setting means sets a sortable particle number for each of the plurality of particles based on the position information acquired by the position information acquisition means.

4. The particle simulation device according to claim 1, wherein
   the workspace is divided into a plurality of cells, and
   the position information acquisition means acquires information indicating a cell in which a particle is positioned, for each of a plurality of particles, as position information.

5. The particle simulation device according to claim 1, wherein
   one of the group consisting of a disaster, a physical problem, and a drug discovery is simulated based on output generated by the particle simulation device.

6. The particle simulation device according to claim 5, wherein
   the disaster is one from the group consisting of a landslide, liquefaction, and a tsunami.

7. The particle simulation device according to claim 1, wherein
   for a performance test in which a static array of particle positions was prepared, an elapsed time taken by the particle simulation device to generate the matrix is less than 5 ms when a particle density is greater than 10 particles per cell.

8. A particle simulation method which is a method of operating a particle simulation device configured to calculate position and velocity of a plurality of particles in a workspace based on interaction force with another particle and simulate behavior of the particles, the particle simulation method comprising:
   a position information acquisition step of acquiring position information indicating a particle position, for each of the plurality of particles;
   a particle number setting step of setting a sortable particle number for each of the plurality of particles;
   a pair setting step of selecting a pair of particles neighboring to each other based on the position information acquired in the position information acquisition step, and setting a pair number for the pair based on the particle number of one of particles of the pair that is set in the particle number setting step;

a reference information generation step of generating a matrix having the pair number set in the pair setting step and the particle numbers of particles of the pair as components of a row, sorting order of a column of the matrix based on the particle number of another particle of the pair, and generating reference information for referring to the pair number of a pair including a particle by the particle number of the particle, based on the sorted matrix;

an interaction force calculation step of performing an interaction determination between particles related to each of pairs selected in the pair setting step and calculating interaction force between particles determined to interact;

a sum calculation step of calculating a sum of interaction forces for each particle from the interaction force calculated in the interaction force calculating step, based on the reference information generated in the reference information generation step; and a particle information calculation step of calculating position and velocity of a particle, based on the sum of interaction forces for each particle that is calculated in the sum calculating step.

9. The particle simulation method according to claim 8, wherein
one of the group consisting of a disaster, a physical problem, and a drug discovery is simulated based on output generated by the particle simulation device.

10. The particle simulation method according to claim 9, wherein
the disaster is one from the group consisting of a landslide, liquefaction, and a tsunami.

11. The particle simulation method according to claim 8, wherein
for a performance test in which a static array of particle positions was prepared, an elapsed time taken by the particle simulation device to generate the matrix is less than 5 ms when a particle density is greater than 10 particles per cell.

12. A non-transitory computer-readable storage medium storing one or more programs for particle simulation, the one or more programs for execution by one or more processors of a computer system, the computer system to function as a particle simulation device configured to calculate position and velocity of a plurality of particles based on interaction force with another particle in a workspace and simulate behavior of the particles, the one or more programs comprising:

position information acquisition means for acquiring position information indicating a particle position, for each of the plurality of particles;

particle number setting means for setting a sortable particle number for each of the plurality of particles;

pair setting means for selecting a pair of particles neighboring to each other based on the position information acquired by the position information acquisition means, and setting a pair number for the pair based on the particle number of one of particles of the pair that is set by the particle number setting means;

reference information generation means for generating a matrix having the pair number set by the pair setting means and the particle numbers of particles of the pair as components of a row, sorting order of a column of the matrix based on the particle number of another particle of the pair, and generating reference information for referring to the pair number of a pair including a particle by the particle number of the particle, based on the sorted matrix;

interaction force calculation means for performing an interaction determination between particles related to each of pairs selected by the pair setting means and calculating interaction force between particles determined to interact;

sum calculation means for calculating a sum of interaction forces for each particle from the interaction force calculated by the interaction force calculation means, based on the reference information generated by the reference information generation means; and particle information calculation means for calculating position and velocity of a particle, based on the sum of interaction forces for each particle that is calculated by the sum calculation means.

13. The non-transitory computer-readable storage medium according to claim 12, wherein
one of the group consisting of a disaster, a physical problem, and a drug discovery is simulated based on output generated by the particle simulation device.

14. The non-transitory computer-readable storage medium according to claim 13, wherein
the disaster is one from the group consisting of a landslide, liquefaction, and a tsunami.

15. The non-transitory computer-readable storage medium according to claim 12, wherein
for a performance test in which a static array of particle positions was prepared, an elapsed time taken by the particle simulation device to generate the matrix is less than 5 ms when a particle density is greater than 10 particles per cell.

* * * * *